United States Patent
Kim et al.

(10) Patent No.: US 8,593,640 B2
(45) Date of Patent: Nov. 26, 2013

(54) OPTICS FOR FORMING A LINEAR BEAM IN OPTICAL COHERENCE TOMOGRAPHY

(75) Inventors: Beop-Min Kim, Wonju-si (KR); Sang-Won Lee, Wonju-si (KR)

(73) Assignees: Industrial-Academic Cooperation Foundation, Yonsei University, Seoul (KR); MTC Medical Co., Ltd., Seoul (KR)

( * ) Notice: Subject to any disclaimer, the term of this patent is extended or adjusted under 35 U.S.C. 154(b) by 656 days.

(21) Appl. No.: 12/682,140

(22) PCT Filed: Oct. 17, 2008

(86) PCT No.: PCT/KR2008/006155
§ 371 (c)(1),
(2), (4) Date: Apr. 8, 2010

(87) PCT Pub. No.: WO2009/051446
PCT Pub. Date: Apr. 23, 2009

(65) Prior Publication Data
US 2010/0220333 A1    Sep. 2, 2010

(30) Foreign Application Priority Data
Oct. 19, 2007    (KR) .......................... 10-2007-0105359

(51) Int. Cl.
*G01B 11/02* (2006.01)
(52) U.S. Cl.
USPC ........................................... 356/497; 356/504

(58) Field of Classification Search
USPC .................................. 356/497, 479, 511, 504
See application file for complete search history.

(56) References Cited

U.S. PATENT DOCUMENTS

| | | |
|---|---|---|
| 2004/0227952 A1 | 11/2004 | Jasapara et al. |
| 2004/0239938 A1 | 12/2004 | Izatt |
| 2006/0055936 A1 * | 3/2006 | Yun et al. ........................ 356/479 |
| 2007/0188765 A1 | 8/2007 | Zhao et al. |
| 2009/0231718 A1 * | 9/2009 | Muenz et al. ................... 359/626 |

OTHER PUBLICATIONS

International Search Report for PCT/KR2008/006155.

* cited by examiner

*Primary Examiner* — Hwa Lee
(74) *Attorney, Agent, or Firm* — LRK Patent Law Firm

(57) ABSTRACT

This invention relates to an optical coherence tomography, in which a light source and an optical linear beam forming system are adopted to obtain two dimensional image of high quality resolution within short time without affection by any mechanical movements. For such purpose, the optical linear beam forming system (20) comprises semicy Under lens (21), convex lens (22) and slit (23) to implement the frequency domain optical coherence tomography. Parallel light beam from the light source is incident on the surface of the semicylinder lens (21), and focal line of the semicylinder lens (21) is located in front of the convex lens (22). The convex lens (22) has short focal point where the parallel light component converges and long focal point where the diverging light component converges. The slit (23) is located between the short focal point and the long focal point.

9 Claims, 3 Drawing Sheets

OPTICS FOR FORMING A LINEAR BEAM IN OPTICAL COHERENCE TOMOGRAPHY

TECHNICAL FIELD

This invention is directed to the frequency domain optical coherence tomography by line scanning scheme using frequency transformation light source, especially to the optical coherence tomography (OCT) in which light is scanned on a subject (or a sample) and reflected light from the subject is received via Line-CCD camera.

BACKGROUND ART

There are two kinds of conventional optical coherence tomographies, time domain OCT and frequency domain OCT, in which dot scanning scheme is adopted using broadband light source and each needs more than one separate scanner. FIG. 1 shows schematic diagram of conventional time domain OCT and FIG. 2 shows that of conventional frequency domain OCT.

In time domain OCT as shown in FIG. 1, light beam coming from a broadband light source (12) is split by an optical splitter (30) into two light beams, which are incident on a reference mirror (50) and a subject and reflected from them, respectively. The reflected light beams are combined at the optical splitter (30), and the optical path length difference between the two light beams gives rise to interference signal (that is, interference pattern). The interference signal is detected by a photo diode (90) and is subject to A/D conversion and demodulation process, resulting in image signal in depth. To obtain two dimensional image, two scanning schemes by movements of both the reference mirror (50) and a scanner (80) have to be accomplished, which is referred as x-z scanning. However these two scanning schemes have difficulties in synchronizing the two movements, take long time in obtaining image, are susceptible to noises by movements of the subject and have low signal to noise ratio (SNR).

In frequency domain OCT as shown in FIG. 2, light beam coming from a broadband light source (12) is, as in the time domain OCT, split by the optical splitter (30) into two light beams, which are incident on the reference mirror (50) and the subject and reflected from them, respectively. The reflected light beams are combined at the optical splitter (30). The combined light beam is detected by a spectroscope (100) and Fourier transformed, resulting in image signal in depth. The frequency domain OCT does not need z-direction scanner and just uses x-direction scanner (80) to obtain two dimensional image. In the frequency domain OCT, higher signal to noise ratio can be obtained than in the time domain OCT. However the frequency domain OCT also have problems that the image is still affected noise by movements of the subject and the spectroscope (100) is to be implemented for detecting the light beam.

DISCLOSURE OF INVENTION

Technical Problem

The object of this invention is to improve the said problems in the conventional OCT and to provide two dimensional image of high resolution within shorter time without mechanical movements of the subject under test by line scanning linear light beam on the subject.

Technical Solution

To achieve the above object, in one aspect of this invention, the optical coherence tomography comprises: a light source (11) emitting light beam with a plurality of wavelengths l1, l2, . . . ln; an optical linear beam forming system (20) forming the linear light beam out of the light beam; an optical splitter (30) splitting the linear light beam coming from the optical linear beam forming system (20) into two light beams, with one light beam directed to a reference mirror (50) and another light beam directed to a subject; two first convex lenses (40), one located between the optical splitter (30) and the reference mirror (50) and another located between the optical splitter (30) and the subject, for collimating the light beams split by the optical splitter (30); second convex lens (60), wherein light beams reflected from the reference mirror (50) and the subject are combined by the optical splitter (30) and the combined light beam is incident on the second convex lens (60); a camera (70) receiving the combined light beams coming from the second convex lens (60); an image processing board detecting signals corresponding to each pixel output by the camera (70); a Fourier transformation section for Fourier transforming the detected signals corresponding to the pixels in terms of the plurality of wavelengths l1, l2, . . . ln to obtain depth-related image information (z-scanning); and a monitor displaying two dimensional image obtained by coupling the pixels along x axis, using the signals output at the Fourier transformation section.

To achieve the above object, in another aspect of this invention, the optical coherence tomography in which light beam coming from a light source is split into two light beams by an optical splitter (30) to be directed to a reference mirror (50) and a subject, the split light beams are collimated by each first convex lenses (40), the two collimated light beams are reflected from the reference mirror (50) and the subject, respectively, to be combined at the optical splitter (30), and the combined light beams are incident on a camera (70) via second convex lens (60), further comprising: an optical linear beam forming system (20) located between the light source and the optical splitter (30) for forming linear light beam to be incident on the optical splitter (30) as the light beam.

To achieve the above object, in further another aspect of this invention, the optical coherence tomography comprises at least: a light source (11) emitting light beam with a plurality of wavelengths l1, l2, . . . ln; a optical linear beam forming system (20) forming linear light beam out of the light beam; an optical splitter (30) splitting the linear light beam coming from the optical linear beam forming system (20) into two light beams, with one light beam directed to a reference mirror (50) and another light beam directed to a subject; two first convex lenses (40), one located between the optical splitter (30) and the reference mirror (50) and another located between the optical splitter (30) and the subject, for collimating the light beams split by the optical splitter (30); second convex lens (60), wherein light beams reflected from the reference mirror (50) and the subject are combined by the optical splitter (30) and the combined light beam is incident on the second convex lens (60); a camera (70) receiving the combined light beams coming from the second convex lens (60).

And in all aspects of this invention, the optical linear beam forming system (20) comprising semicylinder lens (21), convex lens (22) and slit (23).

Parallel light beam coming from the light source is incident on the surface of the semicylinder lens (21), and focal line of the semicylinder lens (21) is located in front of the convex lens (22), resulting in parallel light component and diverging light component to be incident on the convex lens (22).

The convex lens (22) has short focal point where the parallel light component converges and long focal point where the diverging light component converges.

The slit (23) is located between the short focal point and the long focal point, the direction of the slit (23) being parallel to the longitudinal direction of the semicylinder lens (21), resulting in the linear light beam.

To achieve the above object, in further another aspect of this invention, the optical coherence tomography comprises: an optical linear beam forming system (20) including semicylinder lens (21), convex lens (22) and slit (23), wherein parallel light beam coming from the light source is incident on the surface of the semicylinder lens (21), and focal line of the semicylinder lens (21) is located in front of the convex lens (22), resulting in parallel light component and diverging light component to be incident on the convex lens (22), the convex lens (22) has short focal point where the parallel light component converges and long focal point where the diverging light component converges, and the slit (23) is located between the short focal point and the long focal point, the direction of the slit (23) being parallel to the longitudinal direction of the semicylinder (21), resulting in the linear light beam.

Advantageous Effects

According to this invention as aforementioned, the frequency domain optical coherence tomography of this invention uses linear light beam to the subject and can produces two dimensional image using x-z scanning without mechanical movements.

Therefore two dimensional image can be obtained within shorter time with high signal to noise ratio and noise by the movements of the subject can be minimized.

BEST MODE FOR CARRYING OUT THE INVENTION

Figure 3:
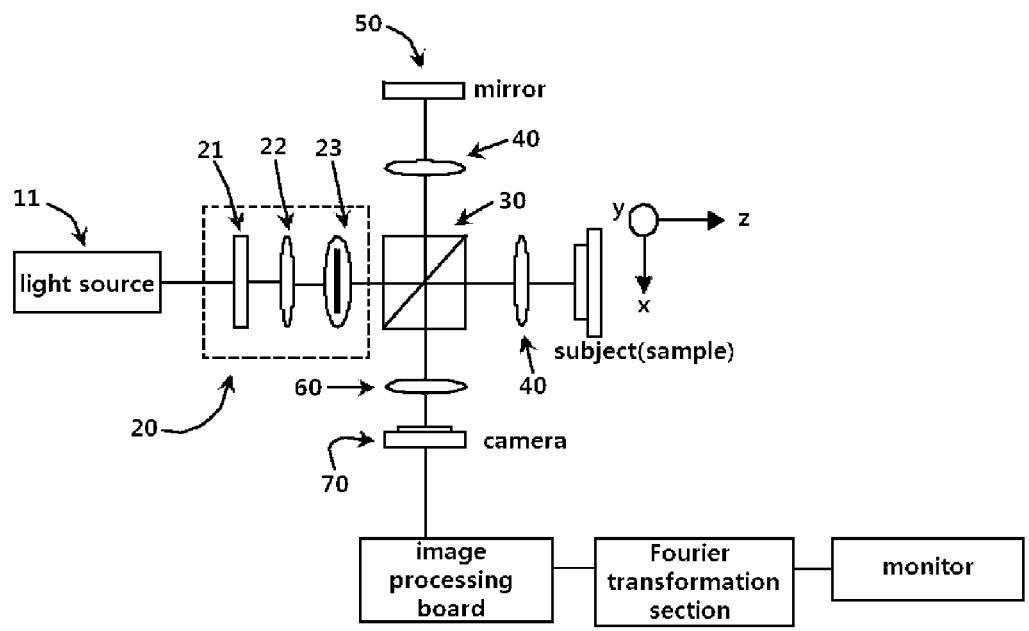
FIG. 3 shows schematic diagram of OCT of this invention using line scanning scheme using wavelength transformation light source.

As showed in FIG. 3, the most preferred type of optical coherence tomography comprises: a light source (11) emitting light with a plurality of wavelengths l1, l2, . . . ln; an optical linear beam forming system (20) forming the linear light beam; an optical splitter (30) splitting the linear light beam coming from the optical linear beam forming system (20) into two light beams, with one light beam directed to a reference mirror (50) and another light beam directed to a subject; two first convex lenses (40), one located between the optical splitter (30) and the reference mirror (50) and another located between the optical splitter (30) and the subject, for collimating the light beams split by the optical splitter (30); second convex lens (60), wherein light beams reflected from the reference mirror (50) and the subject are combined at the optical splitter (30); a camera (70) receiving the combined light beams coming from the second convex lens (60); an image processing board detecting the signals corresponding to each pixel output by the camera (70); a Fourier transformation section for Fourier transforming the detected signals corresponding to the pixels in terms of the plurality of wavelengths l1, l2, . . . ln to obtain depth-related image information (z-scanning); and a monitor displaying two dimensional image obtained by coupling the pixels along x axis, using the signals output at the Fourier transformation section.

MODE FOR THE INVENTION

The configurations and operations of this invention, the optical coherence tomography, will be exemplarily described hereafter in conjunction with the drawings.

FIG. 3 shows schematic diagram of OCT of this invention using line scanning scheme using linear light beam. This OCT comprises a light source (11), an optical linear beam forming system (20), an optical splitter (30), first convex lens (40), reference mirror (50), second convex lens (60), a camera (70), an image processing board, Fourier transformation section and a monitor.

Figure 1:
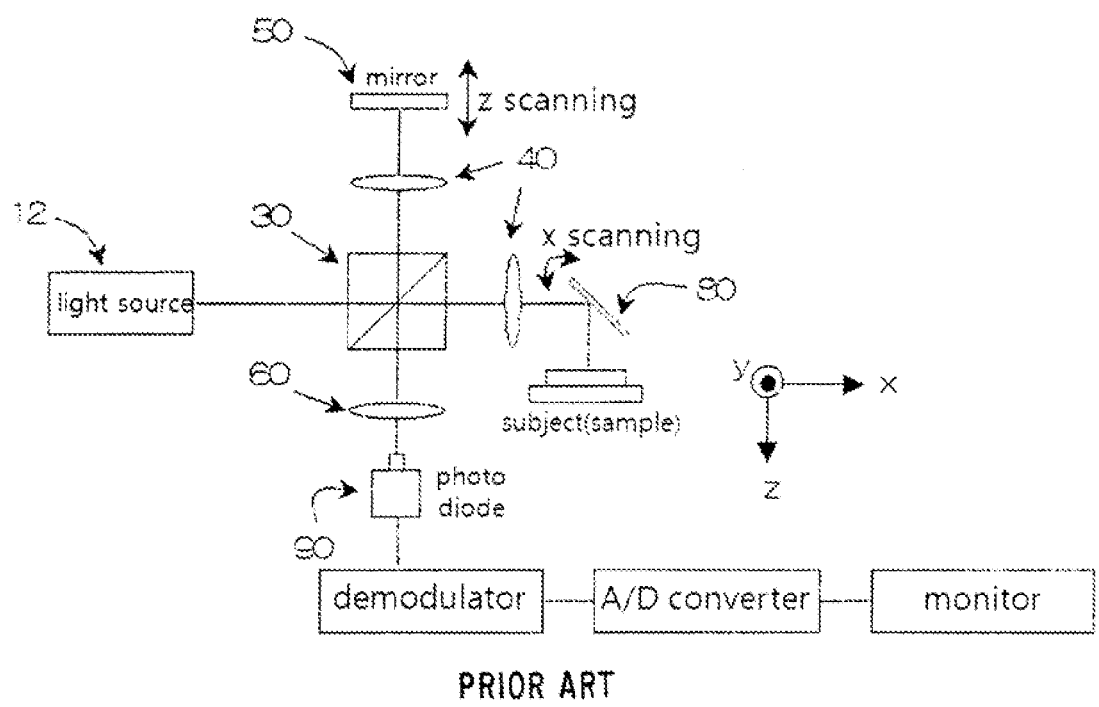
FIG. 1 shows schematic diagram of conventional time domain OCT.
Figure 2:
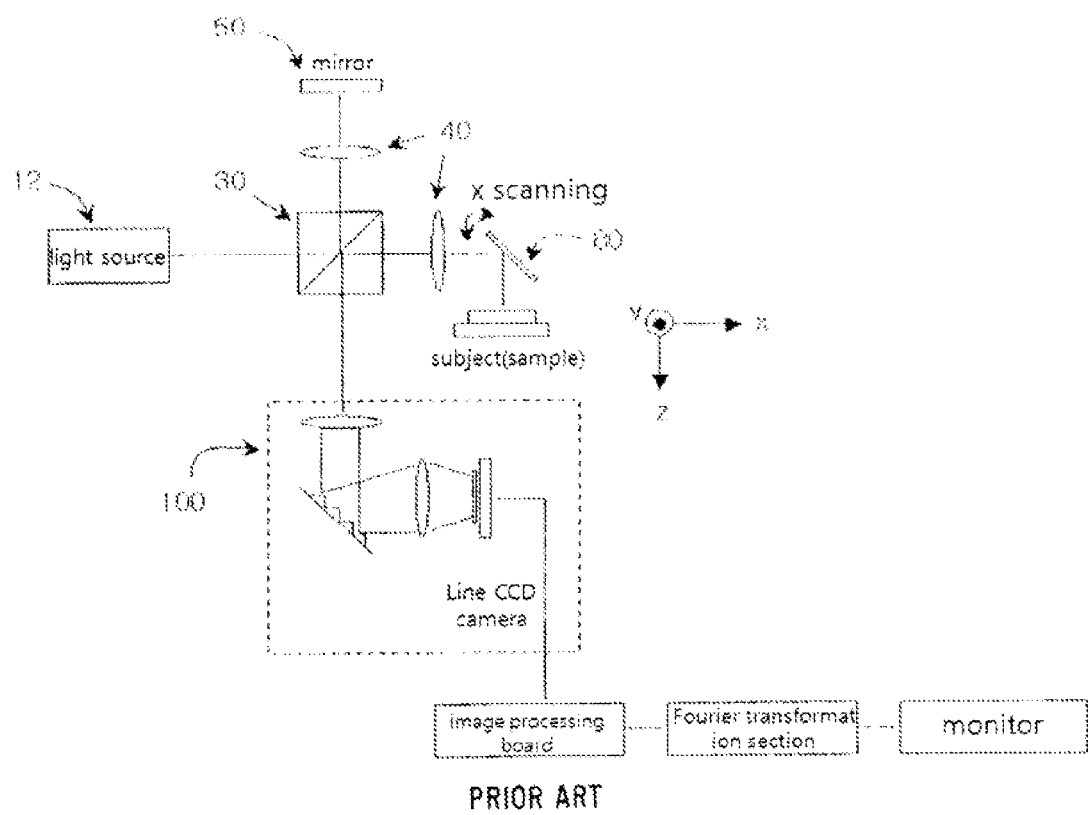
FIG. 2 shows schematic diagram of conventional frequency domain OCT.

The light source (11) generates light beams of wavelengths, l1, l2, . . . ln, sequentially and continuously. Thus the light source plays as similar role as the spectroscope (100) in FIG. 2.

Light beam coming from the light source (11) passes through the optical linear beam forming system (20) which shapes the light beam coming from the light source into linear light beam. The detailed configuration of the optical linear beam forming system (20) will be described hereafter.

The linear light beam is split by the optical splitter (30) into two light beams which propagate to the reference mirror (50) and the subject, respectively. Two first convex lenses (40) collimate the two split light beams to be parallel, respectively. The two parallel light beams are reflected from the reference mirror (50) and the subject and the reflected light beams are combined at the optical splitter (30).

The light beam combined at the optical splitter (30) pass through the second convex lens (60) to be incident on the camera (70). The incident light beam on the camera (70) generates signals per each pixel which are detected by the image processing board.

Image information (z scanning) related with depth of the subject can be obtained by Fourier transformation of the detected light signals of l1, l2, . . . ln, at each pixel. And two dimensional image is obtained by coupling the pixels of the camera along x axis.

Figure 4:
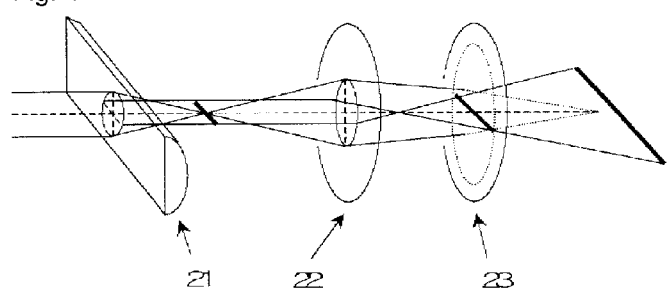
FIG. 4 shows schematic diagram of interior structure of the optical line scanning system of this invention in FIG. 3.

FIG. 4 shows schematic diagram of interior structure of the optical line scanning system of this invention in FIG. 3. The optical line scanning system includes a semicylinder lens (21), a convex lens (22) and slit (23). Thus FIG. 4 shows the detailed diagram of the optical line scanning system adopting the line scanning scheme for this invention.

FIG. 4 shows how the linear light beam is formed. Parallel light beam coming from the wavelength transformation light source (11) is vertically incident on the surface of the semicylinder lens (21), as depicted in FIG. 4. The parallel light beam component incident at the center of the surface along the longitudinal central axis will pass through the semicylinder lens (21) without refraction, resulting in parallel light beam component output from the semicylinder lens (21). The parallel light beam component incident at the position spaced from the longitudinal central axis will converge to a focal line that is drawn with a short dark thick line in the FIG. 4. Thus the parallel light beam incident on the surface of the semicylinder lens (21) is focused on the focal line of the semicylinder lens (21) and after passing through the focal line, the light beam is diverging along the latitudinal direction vertical to the longitudinal axis of the semicylinder lens (21).

The light beam passing through the semicylinder lens (21) is incident on the convex lens (22). The parallel light beam component incident on the convex lens (22) will be focused to short focal point and the diverging light beam component incident on the convex lens (22) will be focused to long focal point, as depicted in FIG. 4.

The slit (23) is located between the short focal point ant the long focal point, as depicted in FIG. 4. The longitudinal direction of the slit is parallel to the direction of the longitudinal central axis of the semicylinder lens (21). The light beam coming from the convex lens (22) passes through the slit (23), resulting in linear light beam, as indicated with a long dark thick line in FIG. 4.

The linear light beam passed through the slit (23) is directed to the optical splitter (30). Thus the linear light beam is incident on the subject and the x scanning process sensitive to mechanical movements of the subject as in the conventional tomography is unnecessary.

Characteristics and advantages of this invention have been set forth. It is understood that the description of the preferred embodiments are, in many respects, only illustrative. Changes may be made in details, particularly in matters of component selection and matters of shape, size and arrangements of parts, without exceeding the scope of this invention. Having described the preferred embodiments in conjunction with the drawings, it can be seen the various purposes and objectives have been achieved, and that there may be modifications and extensions that will become apparent to those skilled in the art without exceeding the spirit and scope of this invention.

INDUSTRIAL APPLICABILITY

According to this invention, the frequency domain optical coherence tomography can be easily implemented by using wavelength transformation light source and the optical line scanning system, and two dimensional image of high quality resolution can be obtained within short time without mechanical movements. The price of the total tomography system can be drastically decreased due to low material cost and simplified process.

Also the tomography of this invention can also be customized for use in various field of medical services including ophthalmology.

The invention claimed is:
1. An optical coherence tomography comprising:
a light source (11) emitting light beam with a plurality of wavelengths l1, l2, . . . , ln;
an optical linear beam forming system (20) forming linear light beam out of the light beam;
an optical splitter (30) splitting the linear light beam coming from the optical linear beam forming system (20) into two light beams, with one light beam directed to a reference mirror (50) and another light beam directed to a subject;
two first convex lenses (40), one located between the optical splitter (30) and the reference mirror (50) and another located between the optical splitter (30) and the subject, for collimating the light beams split by the optical splitter (30);
a second convex lens (60), wherein light beams reflected from the reference mirror (50) and the subject are combined at the optical splitter (30) and the combined light beam is incident on the second convex lens (60);
a camera (70) receiving the combined light beams coming from the second convex lens (60);
an image processing board detecting signals corresponding to each pixel output by the camera (70);

a Fourier transformation section for Fourier transforming the detected signals corresponding to the pixels in terms of the plurality of wavelengths l1, l2, . . . , ln to obtain depth-related image information (z-scanning); and
a monitor displaying two dimensional image obtained by coupling the pixels along x axis, using the signals output at the Fourier transformation section,
wherein the optical linear beam forming system (20) comprises a semicylinder lens (21), a convex lens (22) and a slit (23), and
wherein the slit (23) is located between a short focal point and a long focal point of the convex lens (22), the direction of the slit (23) being parallel to the longitudinal direction of the semicylinder lens (21), resulting in the linear light beam.

2. The optical coherence tomography as claimed in claim 1, wherein parallel light beam coming from the light source is incident on the surface of the semicylinder lens (21), and a focal line of the semicylinder lens (21) is located in front of the convex lens (22), resulting in a parallel light component and diverging light component to be incident on the convex lens (22).

3. The optical coherence tomography as claimed in claim 2, wherein the convex lens (22) has a short focal point where the parallel light component converges and a long focal point where the diverging light component converges.

4. An optical coherence tomography, wherein light bean coming from a light source is split into two light beams by an optical splitter (30) to be directed to a reference mirror (50) and a subject, the split light beams are collimated by each first convex lenses (40), the two collimated light beams are reflected from the reference mirror (50) and the subject, respectively, to be combined at the optical splitter (30), and the combined light beams are incident on a camera (70) via second convex lens (60), the optical coherence tomography comprising:
an optical linear beam forming system (20) located between the light source and the optical splitter (30) for forming linear light beam to be incident on the optical splitter (30) as the light beam,
wherein the optical linear beam forming system (20) comprises a semicylinder lens (21), a convex lens (22) and a slit (23), and
wherein the slit (23) is located between a short focal point and a long focal point of the convex lens (22), the direction of the slit (23) being parallel to the longitudinal direction of the semicylinder lends (21), resulting in the linear light beam.

5. The optical coherence tomography as claimed in claim 4, wherein parallel light beam coming, from the light source is incident on the surface of the semicylinder lens (21), and a focal line of the semicylinder lens (21) is located in front of the convex lens (22), resulting in a parallel light component and a diverging light component to be incident on the convex lens (22).

6. The optical coherence tomography as claimed in claim 5, wherein the convex lens (22) has a short focal point where the parallel light component converges and a long focal point where the diverging light component converges.

7. An optical coherence tomography comprising at least:
a light source (11) emitting light beam with a plurality of wavelengths l1, l2, . . . , ln;
an optical linear beam forming system (20) forming linear light beam out of the light beam;
an optical splitter (30) splitting the linear light beam coming from the optical linear beam forming system (20)

into two light beams, with one light beam directed to a reference mirror (50) and another light beam directed to a subject;

two first convex lenses (40), one located between the optical splitter (30) and the reference mirror (50) and another located between the optical splitter (30) and the subject, for collimating the light beams split by the optical splitter (30);

a second convex lens (60), wherein light beams reflected from the reference mirror (50) and the subject are combined by the optical splitter (30) and the combined light beam is incident on the second convex lens (60); and a camera (70) receiving the combined light beams coming from the second convex lens (60), wherein the optical linear beam forming system (20) comprises a semicylinder lens (21), a convex lens (22) and a slit (23), and wherein the slit (23) is located between a short focal point and a long focal point of the convex lens (22), the direction of the slit (23) being parallel to the longitudinal direction of semicylinder lens (21), resulting in the linear light beam.

8. The optical coherence tomography as claimed in claim 7, wherein parallel light beam coming from the light source is incident on the surface of the sere lens (21), and a focal line of the semicylinder lens (21) is located in front of the convex lens (22), resulting in parallel light component and a diverging light component to be incident on the convex lens (22).

9. The optical coherence tomography as claimed in claim 8, wherein the convex lens (22) has a short focal point where the parallel light component converges and a long focal point where the diverging light component converges.

* * * * *